(12) United States Patent
Volkmuth et al.

(10) Patent No.: US 9,668,687 B2
(45) Date of Patent: Jun. 6, 2017

(54) LANCET MAGAZINE FOR PUNCTURING AIDS

(75) Inventors: Julia Volkmuth, Maxhuette-Haidhof (DE); Michael-Martin Strehl, Pfreimd (DE)

(73) Assignee: Gerresheimer Regensburg GMBH, Regensburg (DE)

( * ) Notice: Subject to any disclaimer, the term of this patent is extended or adjusted under 35 U.S.C. 154(b) by 287 days.

(21) Appl. No.: 14/006,293

(22) PCT Filed: Mar. 28, 2012

(86) PCT No.: PCT/EP2012/055544
§ 371 (c)(1),
(2), (4) Date: Nov. 27, 2013

(87) PCT Pub. No.: WO2012/130899
PCT Pub. Date: Oct. 4, 2012

(65) Prior Publication Data
US 2014/0081173 A1 Mar. 20, 2014

(30) Foreign Application Priority Data

Mar. 30, 2011 (DE) .................. 10 2011 015 656

(51) Int. Cl.
*A61B 5/151* (2006.01)
*A61B 5/15* (2006.01)

(52) U.S. Cl.
CPC ...... *A61B 5/150236* (2013.01); *A61B 5/1513* (2013.01); *A61B 5/150022* (2013.01);
(Continued)

(58) Field of Classification Search
CPC ............ A61B 5/15146; A61B 5/15153; A61B 5/15163; A61B 5/15178; A61B 5/150404;
(Continued)

(56) References Cited

U.S. PATENT DOCUMENTS 4,794,926 A 1/1989 Munsch et al.
5,029,583 A 7/1991 Meserol et al.
(Continued)

FOREIGN PATENT DOCUMENTS

DE 198 55 465 A1 6/1999
EP 0 565 970 10/1993
(Continued)

OTHER PUBLICATIONS

Office Action corresponding to Chinese Patent Application No. 2012800150949, issued Oct. 8, 2014, a related application, 15 pages (with English translation).
(Continued)

*Primary Examiner* — Adam J Eiseman
*Assistant Examiner* — Patrick Fernandes
(74) *Attorney, Agent, or Firm* — Lathrop & Gage LLP

(57) ABSTRACT

The invention relates to a device for storing and supplying lancets for obtaining bodily fluids, the device comprising a lancet magazine having a lancet storage unit for a plurality of needle-shaped lancets and a drive unit for carrying out a piercing process of a lancet, and there being a retraction unit which moves the lancet back from the piercing position to the rest position thereof after the piercing process is carried out.

15 Claims, 11 Drawing Sheets

(52) U.S. Cl.
CPC ...... *A61B 5/15105* (2013.01); *A61B 5/15113* (2013.01); *A61B 5/15117* (2013.01); *A61B 5/15151* (2013.01); *A61B 5/15163* (2013.01); *A61B 5/15176* (2013.01); *A61B 5/150412* (2013.01); *A61B 5/150503* (2013.01); *A61B 5/150526* (2013.01); *A61B 5/150435* (2013.01)

(58) Field of Classification Search
CPC ........ A61B 5/150435; A61B 5/150465; A61B 5/15048; A61B 5/150496; A61B 5/150503; A61B 5/150519; A61B 5/150526; A61B 5/15148; A61B 5/15126–5/15132; A61B 5/15144; A61B 5/15155; A61M 5/3298; A61M 5/322; A61M 5/3221; A61M 5/3232
USPC ......... 606/181–183; 604/110, 156, 157, 196, 604/198
See application file for complete search history.

(56) References Cited

U.S. PATENT DOCUMENTS

| | | | |
|---|---|---|---|
| 5,035,704 | A | 7/1991 | Lambert et al. |
| 5,152,775 | A | 10/1992 | Ruppert |
| 5,578,014 | A | 11/1996 | Erez et al. |
| 8,827,925 | B2 | 9/2014 | Butz et al. |
| 8,828,039 | B2 | 9/2014 | Butz et al. |
| 8,986,258 | B2 | 3/2015 | Michaelis |
| D740,422 | S | 10/2015 | Herfort |
| 9,282,918 | B2* | 3/2016 | Schraga ............... A61B 5/1411 |
| 9,314,200 | B2 | 4/2016 | Vogl et al. |
| 2002/0120216 | A1* | 8/2002 | Fritz .................. A61B 5/15146 600/583 |
| 2004/0260325 | A1* | 12/2004 | Kuhr .................... A61B 5/1411 606/181 |
| 2008/0058849 | A1* | 3/2008 | Conway ............... A61B 5/1411 606/183 |
| 2008/0109024 | A1* | 5/2008 | Berkovitch ........ A61B 5/15146 606/181 |
| 2009/0099478 | A1* | 4/2009 | Cassells ............... A61B 5/1411 600/583 |
| 2009/0281458 | A1* | 11/2009 | Faulkner ............... A61B 5/1411 600/583 |
| 2011/0208091 | A1 | 8/2011 | Butz et al. |
| 2014/0005609 | A1 | 1/2014 | Michaelis |
| 2014/0081173 | A1 | 3/2014 | Volkmuth et al. |
| 2014/0100481 | A1 | 4/2014 | Volkmuth et al. |
| 2014/0100482 | A1 | 4/2014 | Volkmuth et al. |
| 2014/0128897 | A1 | 5/2014 | Butz et al. |
| 2014/0180322 | A1 | 6/2014 | Vogl et al. |

FOREIGN PATENT DOCUMENTS

| | | | |
|---|---|---|---|
| EP | 1 190 674 A2 | 3/2002 | |
| WO | WO 2005107595 A1 * | 11/2005 | ........... A61B 5/1411 |
| WO | WO 2008/140464 A2 | 11/2008 | |

OTHER PUBLICATIONS

International Preliminary Report on Patentability, International Application No. PCT/EP2012/055544, English translation, Oct. 2, 2013, 7 pages.
International Preliminary Report on Patentability, International Application No. PCT/EP2012/055544, German, 5 pages.
International Search Report and Written Opinion, International Application No. PCT/EP2012/055544, German Language, Jul. 5, 2012, 11 pages.
International Search Report, International Application No. PCT/EP2012/055544, English Language, Jul. 5, 2012, 2 pages.

* cited by examiner

LANCET MAGAZINE FOR PUNCTURING AIDS

CROSS REFERENCE TO RELATED APPLICATIONS

This application is a U.S. National Stage Application under 35 U.S.C. §371 of International Application No. PCT/EP2012/055544, filed Mar. 28, 2012, which claims the benefit of and priority to German Application No. 10 2011 015 656.9, filed on Mar. 30, 2011, each of which is hereby incorporated by reference in its entirety.

DESCRIPTION

The invention relates to a device for storing and supplying lancets for obtaining bodily fluids, the device comprising a lancet magazine having a lancet storage unit for a plurality of needle-shaped lancets and a drive unit for carrying out a piercing process of a lancet, and there being a retraction unit which moves the lancet back from the piercing position to the rest position thereof after the piercing process has been carried out.

Devices of this type for storing and supplying lancets are preferably used for analysing samples of bodily fluids, in particular blood samples. In clinical diagnosis, this analysis makes early and reliable detection of pathological conditions possible, as well as selective and well-founded monitoring of bodily conditions. In this context, medical blood diagnostics always assumes that a blood sample is obtained from the individual to be analysed. Whilst in clinics and at registered doctors several millilitres of the blood of a person to be analysed are often taken for analysis by way of a vein puncture, so as to be able to carry out a plurality of laboratory tests, nowadays a few microlitres of blood or even less are often sufficient for a single analysis which is selectively directed towards one parameter. For this purpose, for obtaining blood through the skin, it is sufficient to pierce for example the fingertip or the earlobe of the person to be analysed by the aid of a sterile, sharp lancet, so as to obtain a few microlitres of blood or even amounts of blood in the nanolitre range for the analysis. This method is primarily suitable when it is possible to analyse the blood sample immediately after obtaining the blood.

In particular when medical laymen carry out simple analyses of the blood themselves, and when blood is to be obtained regularly several times a day by diabetics for monitoring blood glucose concentration, lancets and blood taking devices, blood lancet devices or piercing aids adapted thereto are provided, which make it possible to obtain blood in as painless and reproducible a manner as possible. Lancets and piercing aids of this type are disclosed for example in EP A 0 5650970.

In the systems which are currently commercially available, the lancets are prepared for the use of piercing aids in a loose form, or what are known as single-use piercing aids are used, which comprise a single lancet and are subsequently thrown away or at least cleaned. To prepare the lancet in a loose form, before each piercing process the user takes a lancet out of a packet containing a plurality of lancets. Subsequently, the piercing aid is prepared for receiving the lancet, the lancet holder of the piercing aid being exposed. The lancet which has been taken from the packet is manually inserted into and fixed in the lancet holder of the piercing aid. The protective casing of the lancet must then be removed manually. Subsequently, the piercing aid has to be sealed again using the cap thereof. The cap ensures that the lancet is no longer accessible from the outside. It generally has one opening, through which the lancet tip can exit during the actual piercing process. Finally, the piercing aid is gripped and is available for the piercing process for obtaining blood.

The large number of manual operating steps for conventional lancet systems is perceived by the user as disadvantageous and is especially problematic in the case of limited perception in a hypoglycaemia condition. In addition, once a lancet has been inserted, there is nothing preventing the user from using it repeatedly for piercing and obtaining blood, which results in the hygiene aspects being neglected.

U.S. Pat. No. 5,152,775, U.S. Pat. No. 4,794,926 and U.S. Pat. No. 5,035,704 disclose piercing aids which store a plurality of lancets therein and can use them individually in succession for piercing processes. After the piercing process, the lancets can be removed from the device individually. The magazining and the possible automated supply of the lancets help to prevent errors when inserting the lancet into a piercing aid. To carry out the piercing movement, the lancet in the piercing aid initially has to be moved or deflected in a piercing direction and subsequently retracted into the starting position thereof as rapidly as possible. The needle or lancet respectively thus has to be moved both forwards in the piercing direction and back into the starting position. An automatic change of lancet can only be carried out with difficulty in a system of this type. In addition, lancets of this type comprise a lancet body which is adapted to the lancet holder and which produces a rigid connection between the lancet and the holder, so as to ensure in particular the rearward movement. As a result, lancets of this type are often voluminous, and storing them in a magazine often leads to large dimensions of the lancet system as a whole.

U.S. Pat. No. 5,578,014 discloses a lancet system in which the drive of the lancet for the forward movement operates independently of the drive for the rearward movement. The forward movement is brought about by a spring-driven plunger, which is part of a piercing aid and acts on the lancet from behind, that is to say from the side thereof remote from the tip. The rearward movement is driven by a spring which is contained in the lancet. Similar systems are described in U.S. Pat. No. 5,029,583 and DE-A 198,55,465. In this context, a drawback is that each lancet has to be equipped with its own spring, what makes them complicated and expensive to produce. In addition, it is only possible with difficulty to miniaturise the entire system.

The fact that the manufacturing costs are high for lancets of this type, which are of course mass-produced items for single use, is also undesirable.

The object of the invention is therefore to provide a device for storing and supplying lancets for obtaining bodily fluids which makes it possible to arrange a large number of lancets, which can be produced cost-effectively, in a small space, and is of a simple overall construction and thus operates reliably.

This object is achieved by way of the features of claim 1.

The central idea behind the invention is that in a device for storing and supplying lancets for obtaining bodily fluids the device comprises the following:

a lancet magazine, which comprises a lancet storage unit, preferably substantially in the form of a cylindrical shell or a disc or rectangle or some other form and having a plurality of substantially needle-shaped lancets, and a drive unit, which moves a selected lancet for carrying out a piercing process from a rest position into a piercing position in a piercing direction, and a retraction unit, which moves the selected lancet from the piercing position into the rest position thereof after the piercing process has been carried out, the retraction unit being connected to the lancet storage unit and being displaceable with respect thereto, and the drive unit being fixed with respect to the retraction unit as seen in the piercing direction.

A device of this type for storing and supplying lancets for obtaining bodily fluids advantageously makes it possible to access individual lancets, which are arranged in the lancet storage unit, in succession in a compact manner with cost-effective manufacture and simple operation, and to retract them again rapidly, after the forward movement of an individual lancet for carrying out a piercing process, by way of the retraction unit, which is rigidly connected to the drive unit, without the retraction unit having to be pivoted or slid into the engagement position, in addition to the engagement in the lancet, for the retraction process. Instead, the retraction unit is displaced forwards together with the drive unit during the forward movement, and slid back again, by loading with spring force or electromagnetic force or some other force from the drive unit, so as to retract the lance from the body again. This also makes it unnecessary to arrange a spring on each individual lancet. In addition, lancets can be used which do not comprise a plastics material enclosure which is rigidly connected to the individual lancet in each case.

In accordance with a preferred embodiment, the lancet storage unit in the form of a cylindrical shell, in which the lancets are arranged distributed mutually parallel on the circular path and extend substantially in the longitudinal axis of the cylindrical shell, encloses the retraction unit, which is substantially cylindrical in form. The retraction unit is enclosed or encompassed at least in part and ensures that the retraction unit can be arranged compactly inside the cylinder shell of the lancet storage unit and can be displaceable.

The drive unit comprises at least one plunger-like element, the plunger end of which touches the end of the selected lancet during the piercing process and displaces it in the piercing direction inside the lancet storage device. In this context, the plunger-like element is also suitable for displacing the retraction unit with respect to the lancet storage unit. This applies both in the forward and in the rearward direction, that is to say during the piercing process for the displacement of the lancet into and out of the skin of a human body.

In accordance with the preferred embodiment thereof, each lancet is arranged inside the lancet storage unit, which is in the form of a cylindrical shell, in a separate continuous duct, which preferably extends in the longitudinal direction, that is to say along the longitudinal axis of the cylinder shell of the lancet storage unit. There are thus a number of continuous ducts, which are arranged on a circular path in the cylinder shell of the lancet storage unit, it being possible to actuate and displace the needles individually by way of the plunger-like element.

In accordance with a preferred embodiment, the lancets do not comprise plastics material enclosures which are rigidly fixed thereto, but each merely have a curved end so as each to engage in a depression, extending in the radial direction, on the end face of the partially cylindrical retraction unit. In this way, the face and the depressions arranged therein of the retraction unit can be used for moving the lancet back out of the human body again during a retraction process, that is to say during a movement of the individual lancet in the rearward direction, in a rapid and simple manner by displacing the retraction unit back.

In accordance with a development of the invention, a first clip connection or another type of positive, non-positive or material connection is provided which connects the drive unit in the form of a plunger-like element to the retraction unit rigidly as seen in the piercing direction. This first clip connection is suitable for twisting the plunger-like element with respect to the retraction unit about a longitudinal axis, extending in the piercing direction, of the lancet magazine. The clip connection is thus used for rigidly connecting the retraction unit to the drive unit, and in particular to the plunger-like element, in the displacement direction or respectively piercing direction both in the forward and in the rearward direction, the plunger element being twisted with respect to the retraction unit so as to select the next lancet for subsequently touching the plunger-like element with the end of the lancet. A first clip connection of this type is advantageously arranged between a cylinder portion of the plunger-like element and the inside of the retraction unit inside which the cylinder portion is located. It consists of at least one, preferably two or three projections, which can be resiliently deflected by means of at least one plastics material arm and engage in a channel formed so as to be complementary thereto. The channel can be attached to the cylinder shell of the plunger-like element and the projections can be fixed to the retraction unit, or vice versa.

A second clip connection, which holds the retraction unit in a particular displacement position with respect to the lance storage unit in the case of a rest position of all the lancets, serves to arrange the retraction unit in the inserted position inside the lancet storage unit in the rest position until a further trigger from the user makes it possible to displace the retraction unit forwards in the piercing direction again together with the selected lancet.

The drive unit can be loaded with spring force by means of at least one spring element, so as to move the plunger-like element and the retraction unit in and counter to the piercing direction. This makes spring arrangements on the individual lancets, or else on the retraction unit itself, unnecessary. Instead, the drive unit can drive the entire forward and backward movement, making it possible to change the lancet magazine in its entirety and to connect a new lancet magazine with the drive unit without individual drive elements having to be present inside the lancet magazine. This makes a simple and cost-effective construction of the lancet magazine possible, without any springs or similar elements being arranged. Electromagnetic drives or other force-loaded drives are also conceivable.

Further advantageous embodiments may be taken from the following descriptions in connection with the drawings, in which.

Figure 1:
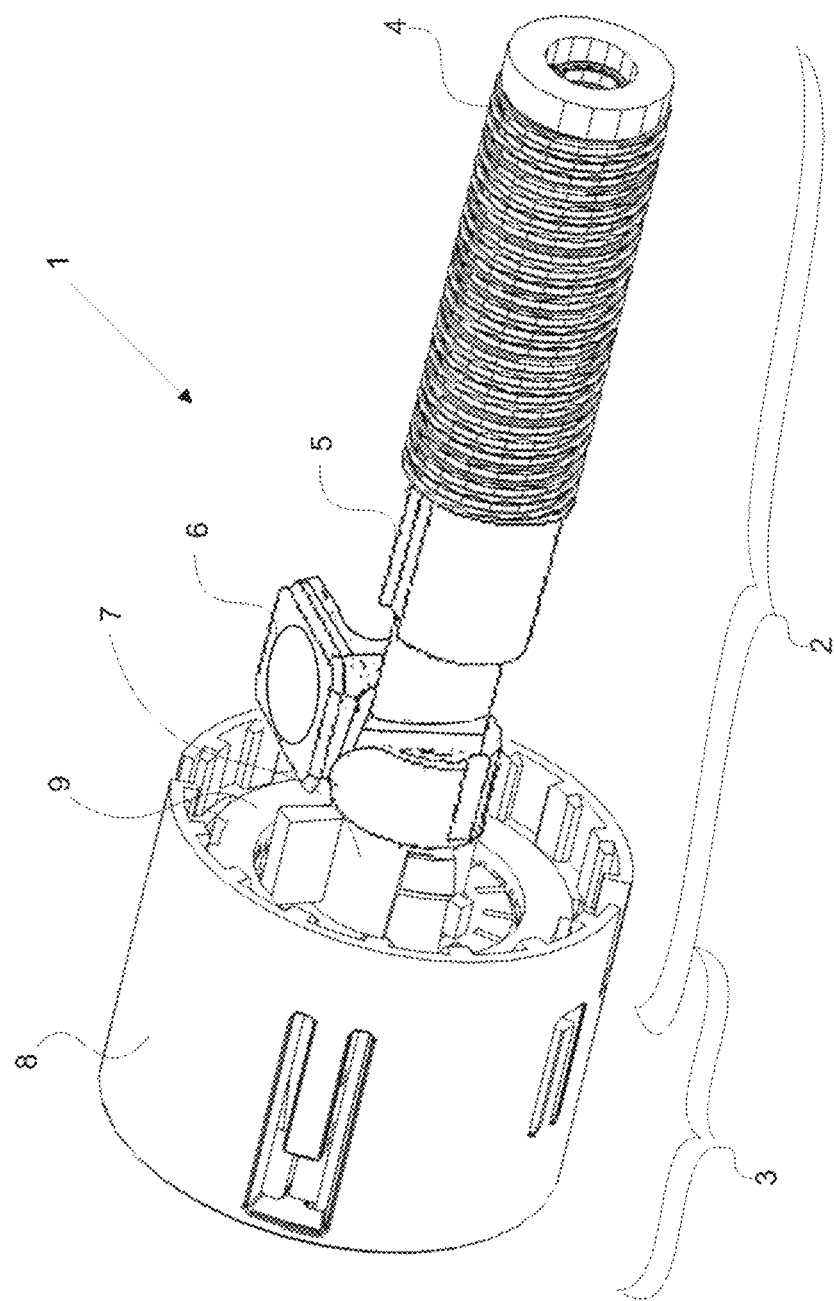
FIG. 1 is a perspective view of a base construction of the device according to the invention in accordance with one embodiment of the invention.

FIG. 1 is a perspective view of the basic structure, without further cover elements, of the entire device according to the invention for storing and supplying lancets for obtaining bodily fluids. This device 1 comprises a drive unit 2 and a lancet magazine 3, the drive unit 2 comprising a spring, preferably a spiral spring 4, which serves to load, with spring force, a plunger 7 which moves in the forward and rearward direction, the spiral spring 4 being arranged around a cylinder 5. A trigger unit 6 serves to allow the drive unit, in particular the plunger 7, to move forwards, that is to say towards the lancet magazine exit at the lower end (left side of the drawing), and subsequently in the rearward direction. This trigger unit 6 is preferably arranged as a push-button.

The lancet magazine 3 comprises an outer housing 8 together with a retraction unit 9.

Figure 2:
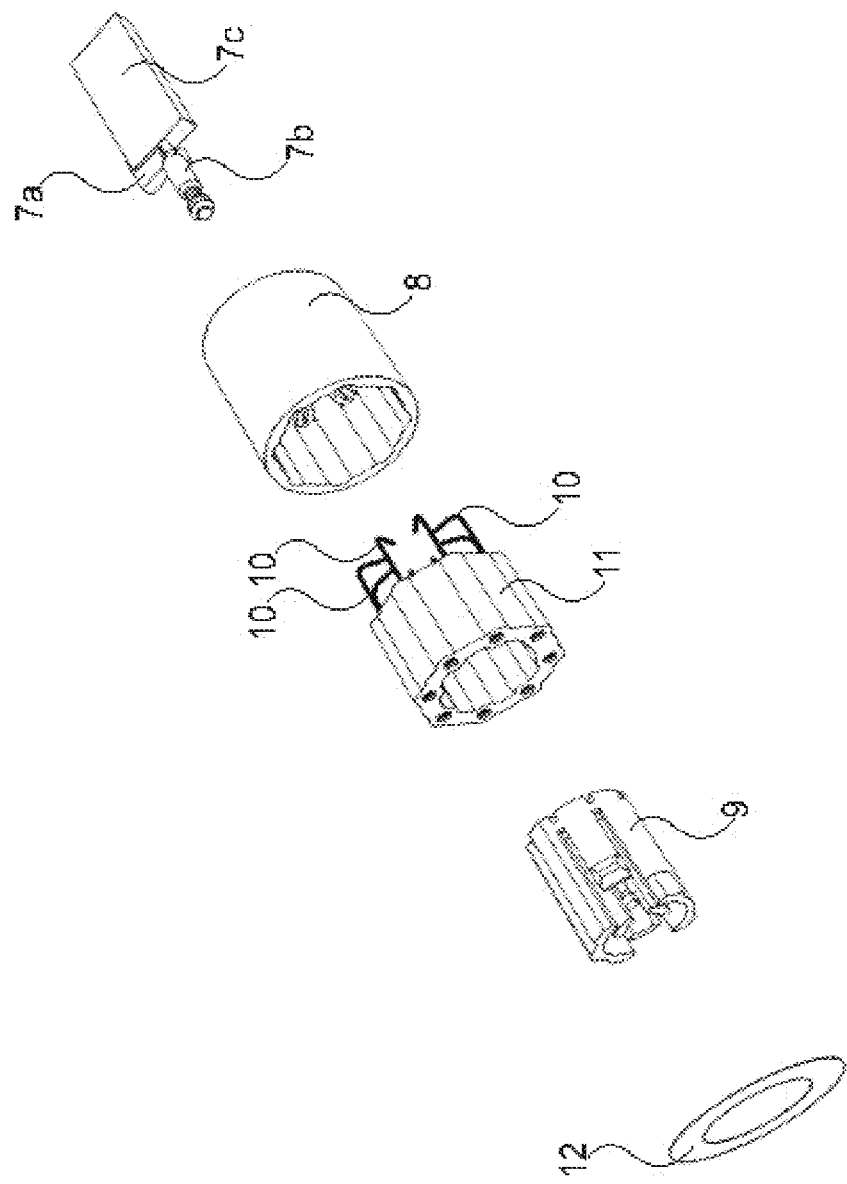
FIG. 2 is an exploded view of individual parts of the device according to the invention.

FIG. 2 is an exploded view of parts of the embodiment of the device, in particular of the lancet magazine of the device according to the invention. From this drawing, it can be seen that the cylindrically constructed housing comprises the retraction unit 9 and a lancet storage unit 11 in the form of a cylindrical shell. In this lancet storage unit 11, a plurality of lancets 10 are arranged inside the shell, and said lancets are formed in a curved manner at the upper ends thereof so as to be able to allow the retraction unit 9, which is displaceable inside the lancet storage unit 11, to engage therein.

Facing downwards, the lancet magazine comprises a terminal cover 12, which is of course configured in such a way that the lancets can still exit the lancet storage unit 11 downwards.

The drive unit 2 comprises the plunger 7, from which a plunger-like element 7a can act on individual lancets in the upper end regions thereof and thus cause the individual lancets to be displaced downwards so as to exit the lancet magazine. The plunger 7 further comprises a cylindrical portion 7b for fastening a base element 7c of the plunger 7 to the retraction unit 9.

Figure 3:
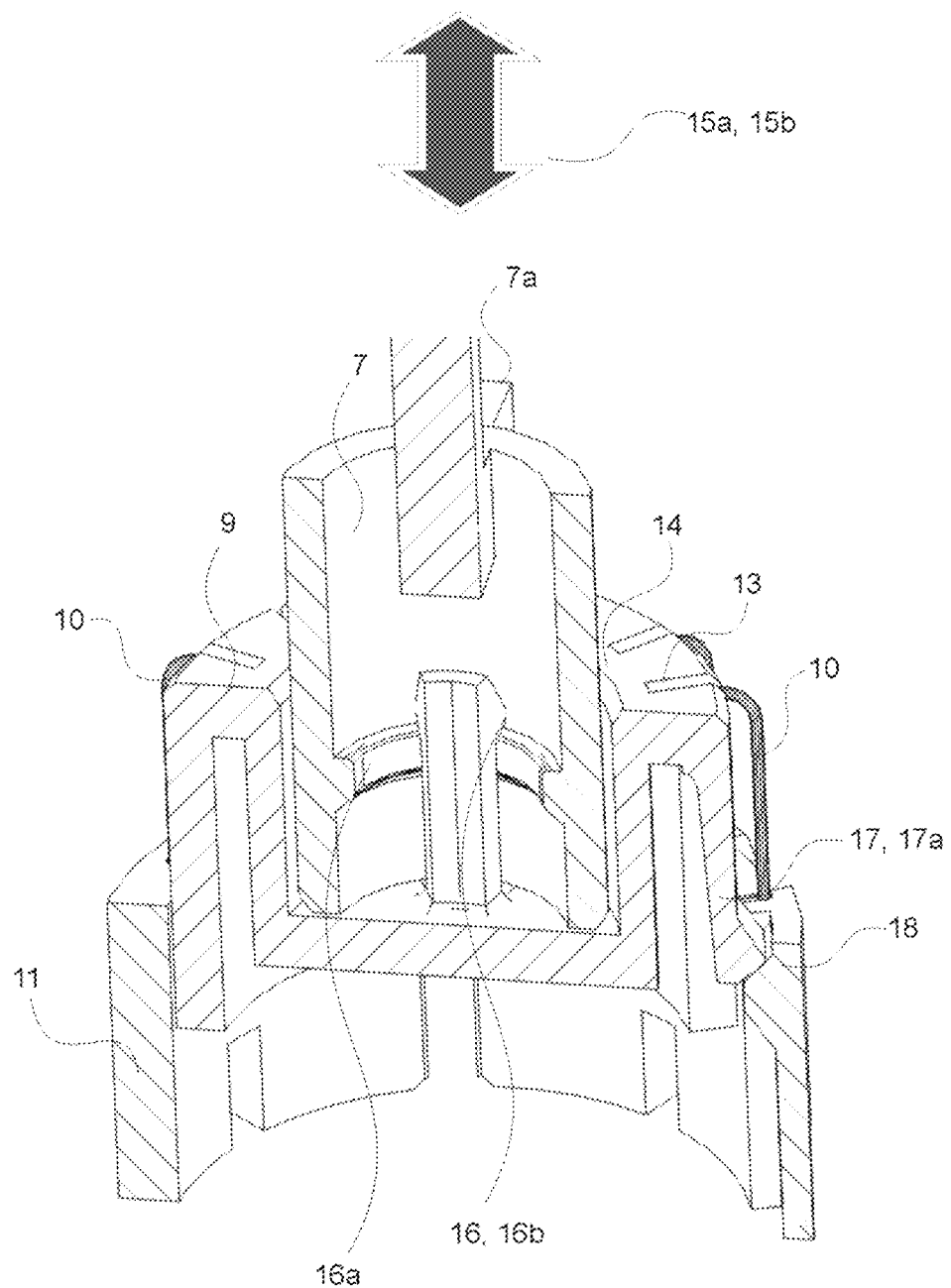
FIG. 3 is a sectional view of the lancet magazine, together with parts of the drive unit of the device according to the invention.

FIG. 3 is a sectional drawing of the lancet magazine together with parts of the drive unit of the device according to the invention. In this drawing, it can clearly be seen that the plunger 7 is connected to the retraction unit 9 by means of a first clip connection 16, 16a, 16b the clip-like projection 16a being arranged on the retraction unit 9, a channel or a projection 16 being present on the inside of the cylinder shell of the plunger 7. Thus, by means of the first clip connection, the plunger 7 can be rotated about the longitudinal axis thereof and about the longitudinal axis of the device as a whole, and thus also of the lancet magazine, but is fixed in the direction of the longitudinal axis or respectively rigidly connected to the retraction unit 9. Of course, clip-like projections of this type, which can be arranged individually or in a plurality on a circular path, may also be connected to the plunger 7 and there may be a channel of a corresponding complementary form or a circular projection on the retraction unit 9.

The lancets 10 are arranged in the cylinder shell of the lancet storage unit 11 in such a way that in each case the upper end thereof engages in a radially orientated depression 13 within a surface 14 of the retraction unit 9.

A second clip connection 17, 17a, 18 is arranged between the retraction unit and the lancet storage unit, one or more clip-like projections 17a being connected to the retraction unit and a projection 18 of a complementary form or a channel, in which the clip-like projection 17a can engage, being provided circularly on the inside of the lancet storage unit.

Thus, the second clip connection, which is adapted so as to connect the retraction unit 9 non-permanently to the lancet storage unit 11 in the longitudinal direction of the device as a whole, can serve, in a rest position in which the retraction unit 9 is displaced upwards inside the lancet storage unit 11 and none of the lancets is exiting the lower end of the lancet storage unit, to maintain a fastening of the retraction unit 9 inside the lancet storage unit 11 which is to be overcome by compression. This is to ensure that the retraction unit reliably holds all of the lancets inside the lancet storage unit 11 as long as a rest position is present. In this case, during a piercing process, both the plunger 7, comprising the plunger-like element 7a, which acts on one of the lancets, and the retraction unit 9 would be slid briefly downwards in the forward or piercing direction 15a and upwards in the rearward or retraction direction 15b, in accordance with the double-headed arrow 15a 15b. This results in one of the selected lancets rapidly sliding forwards and back, and makes the piercing process possible.

Figure 4:
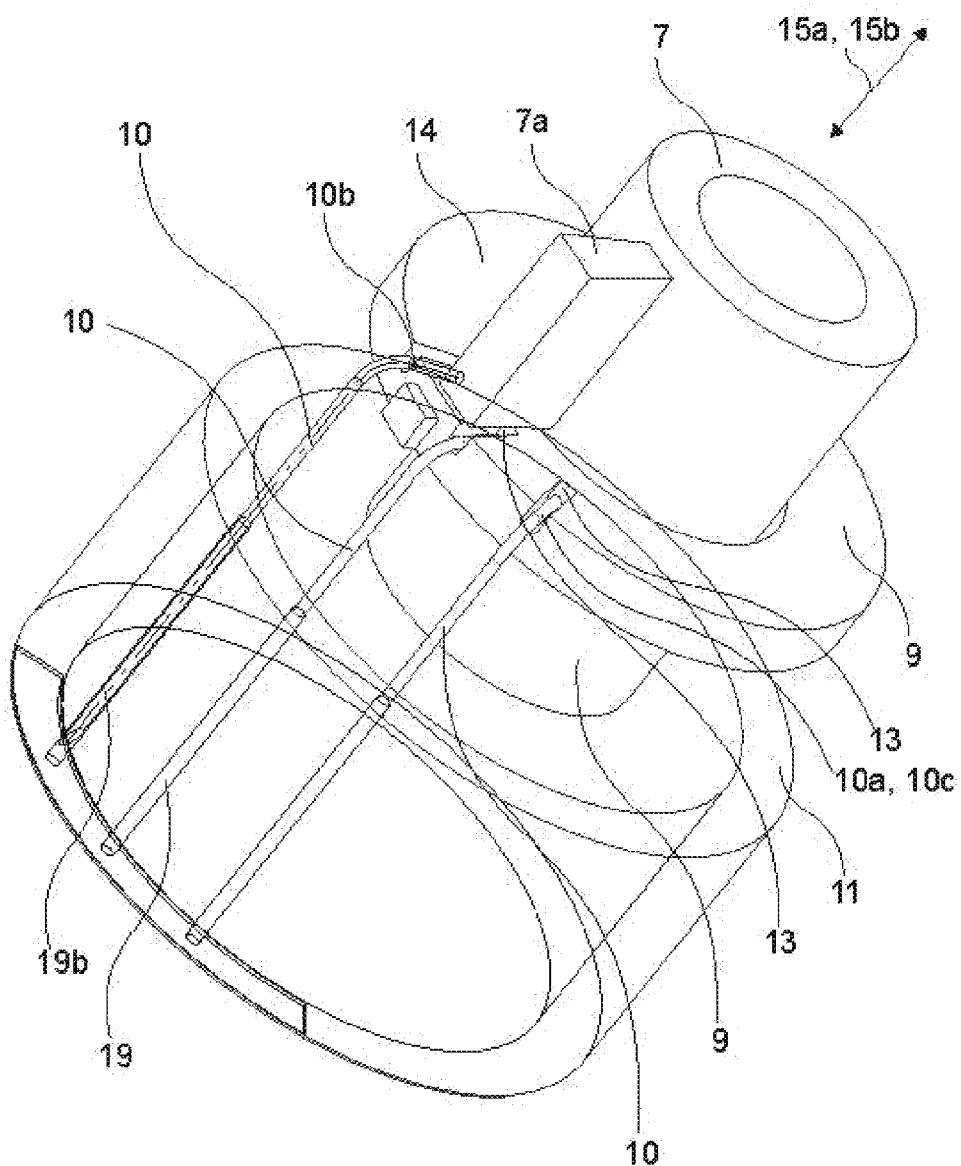
FIG. 4 is a schematic further drawing of the lancet magazine together with parts of the drive unit, with the lancets not being extended, in accordance with one embodiment of the present invention.

FIG. 4 is a schematic further drawing of the lancet magazine together with parts of the drive unit of the device according to the invention. From this drawing, by comparison with the drawing of FIG. 5, the basic operation of the device can be seen. From comparing the drawings of FIG. 4 and FIG. 5, it is clear that the lower end of the plunger-like element 7a acts on a selected lancet 10b, which is arranged inside one of the depressions on the surface 14 of the retraction unit 9. This lancet comprises a curve at the upper end 10c thereof, and thus results in a curved end 10a, as with the other lancets. This makes engagement in the depressions 13 on the surface 14 possible.

Figure 5:
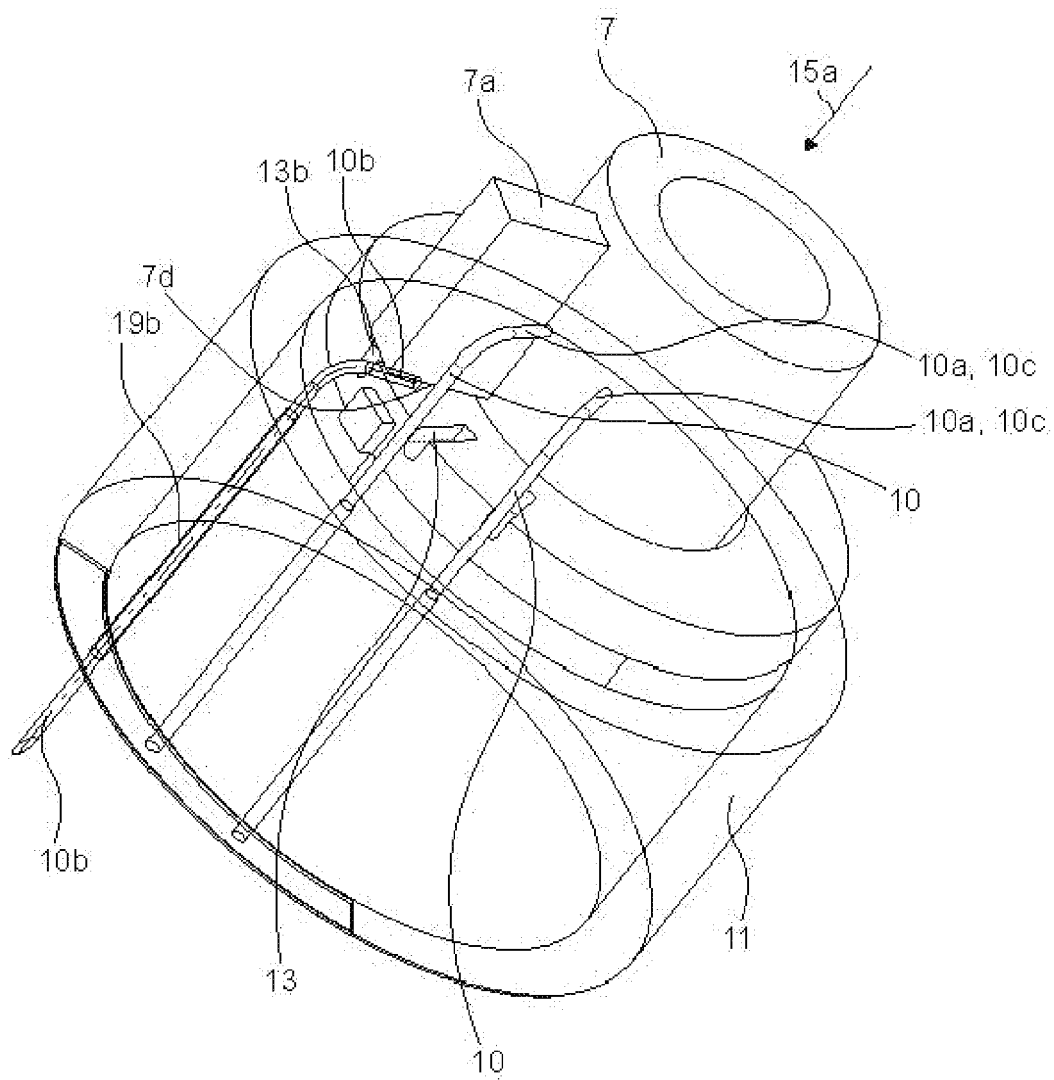
FIG. 5 is a schematic further drawing of the lancet magazine together with parts of the drive unit, with a lancet being extended, in accordance with one embodiment of the present invention.

FIG. 4 and FIG. 5 merely show three lancets, but more than three lancets may be arranged in a circle along the cylindrical shell of the lancet storage unit 11.

During downward displacement of the drive unit or plunger 7 respectively and thus of the plunger-like element 7a in accordance with the arrow 15a, a lower end 7d touches the upper end 10c of the selected lancet 10b and pushes the lancet downwards inside a continuous duct 19b, which is also present for the remaining lancets 10 and is marked with reference numeral 19, until the tip of the lancet exits at the lower end of the lancet storage unit 11. The upper end 10c of the selected lancet 10b remains inside a depression 13b in the surface 14 of the retraction unit during this forwards movement, and is displaced downwards together with the retraction unit 9. Subsequently, as a result of the drive unit 2 (not shown in greater detail here) being loaded with spring force, the retraction unit as a whole moves backwards together with the individual selected lancet 10b until it enters the lancet storage unit again at the lower end of the lancet storage unit. Meanwhile, the remaining lancets 10 having upper ends 10c 10a remain in the previous position inside the lancet storage unit 11, and are not displaced inside the continuous ducts 19. This can be seen clearly from FIG. 5.

Figure 6:
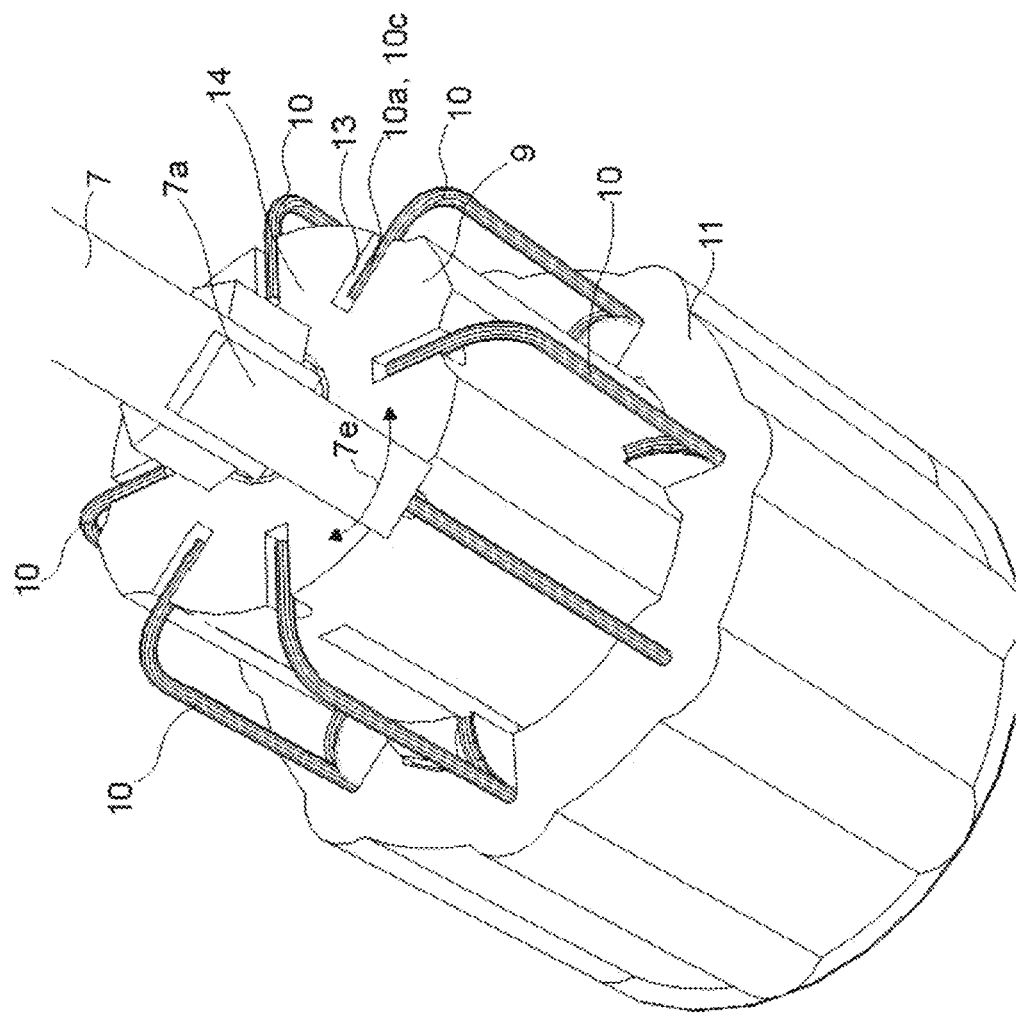
FIG. 6 is a perspective view of the lancet magazine with parts of the drive unit from diagonally above, without an outer housing.

FIG. 6 is a schematic drawing of the lancet magazine, without cover parts, together with parts of the drive unit from diagonally above. From this drawing, it can be seen that the individual lancets 10 are arranged in a circle inside the lancet storage unit 11 and are held in position by the retraction unit 9 until the retraction unit 9 is displaced downwards inside the lancet storage unit 11. This takes place in a known manner by means of the plunger-like element 7a.

The plunger-like element 7a—as shown by the double-headed arrow 7e—can be rotated about a longitudinal axis of the device and of the lancet magazine, in such a way that the underside 7d of the plunger-like element 7a can approach individual lancets and a new lancet can thus be selected.

Figure 7:
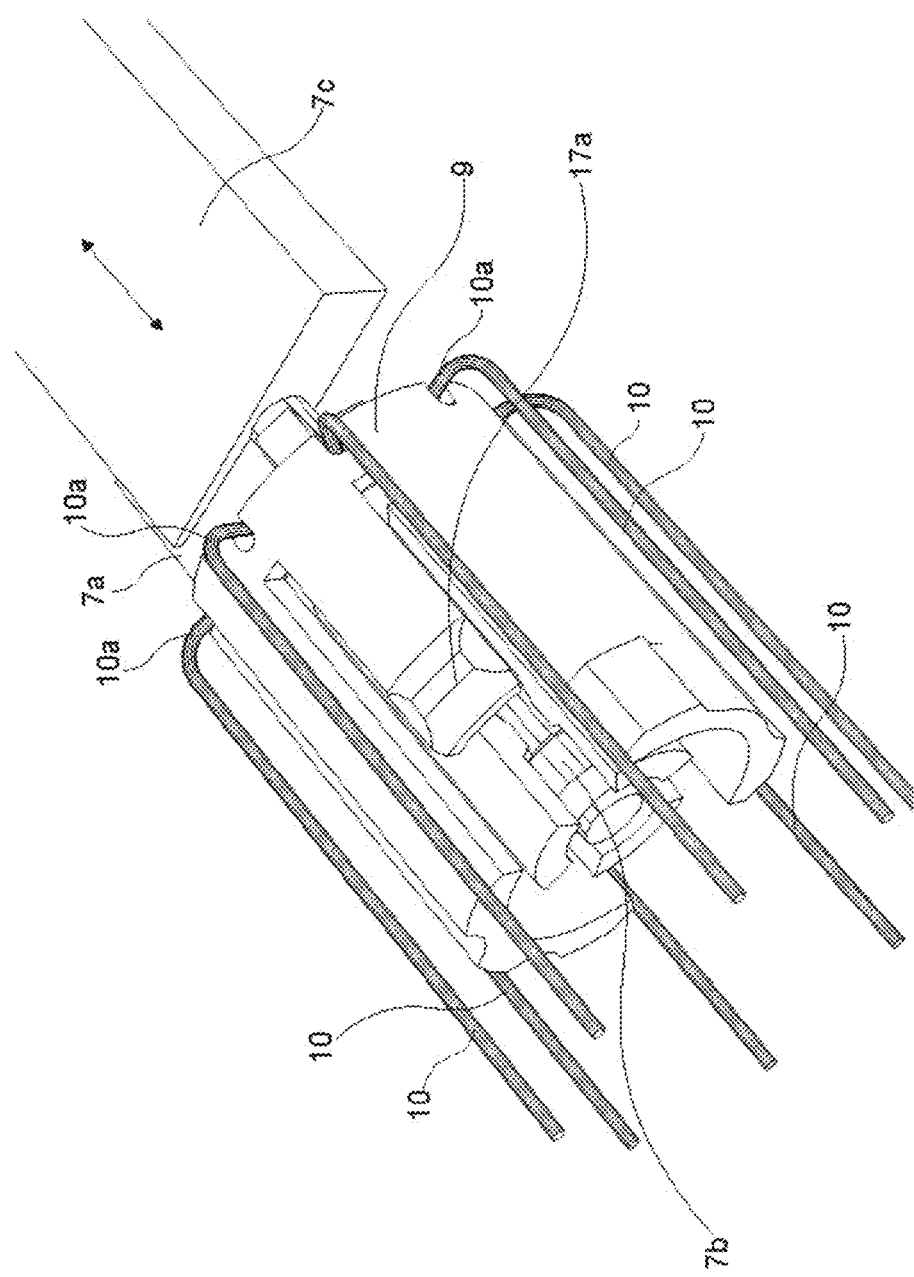
FIG. 7 is a perspective view of parts of the lancet magazine together with parts of the drive unit in a view from diagonally below.

FIG. 7 shows parts of the lancet magazine together with parts of the drive unit of the device according to the invention. In this drawing, the lancet storage unit in which the lancets are arranged is not shown. Instead, merely the retraction unit 9 is shown, and engages, by means of a clip connection 17, in a channel of a complementary form or a projection (not shown here) of the lancet storage unit which encloses or respectively encompasses this retraction unit 9.

Figure 8:
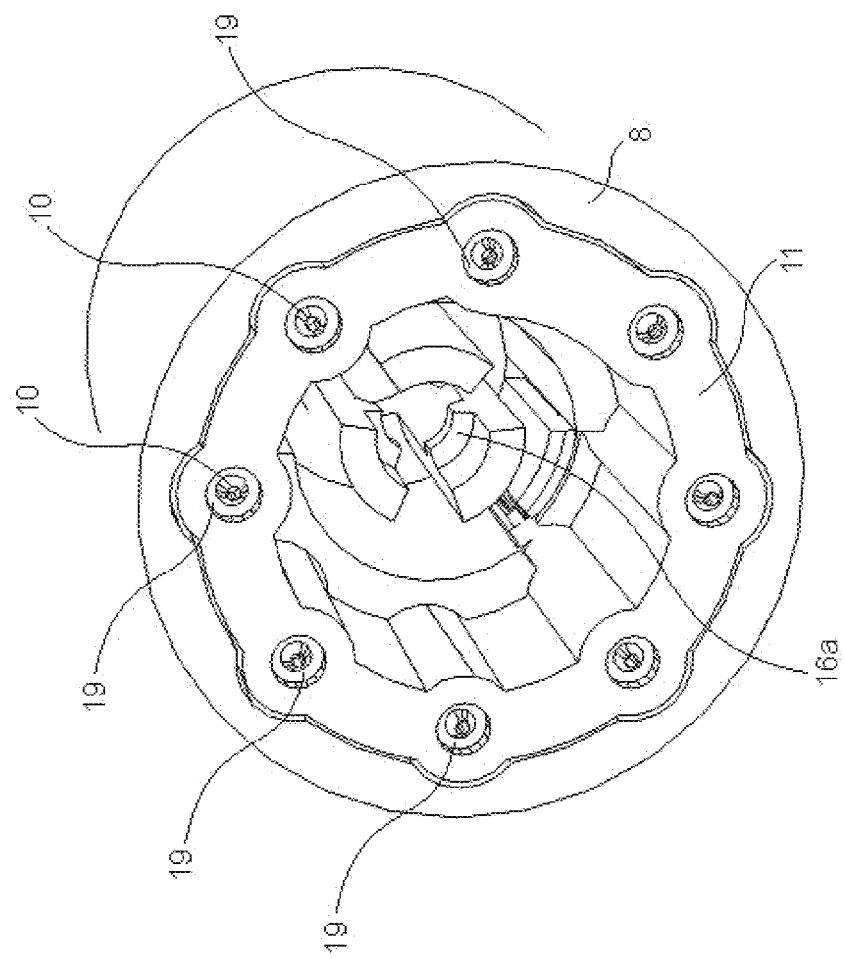
FIG. 8 is a perspective view of the lancet magazine of the device according to the invention in a perspective view from diagonally below.

FIG. 8 is a perspective view of the lancet magazine in the device according to the invention from below. From this drawing, it can be seen that the individual lancet tips of the lancets 10 are arranged in exit openings of the continuous ducts 19. In addition, from the first clip connection a total of three clip-like projections 16a can be seen, which engage in an indentation (not shown in greater detail here), channel or projection of the cylinder-like portion 7b of the plunger 7.

Figure 9:
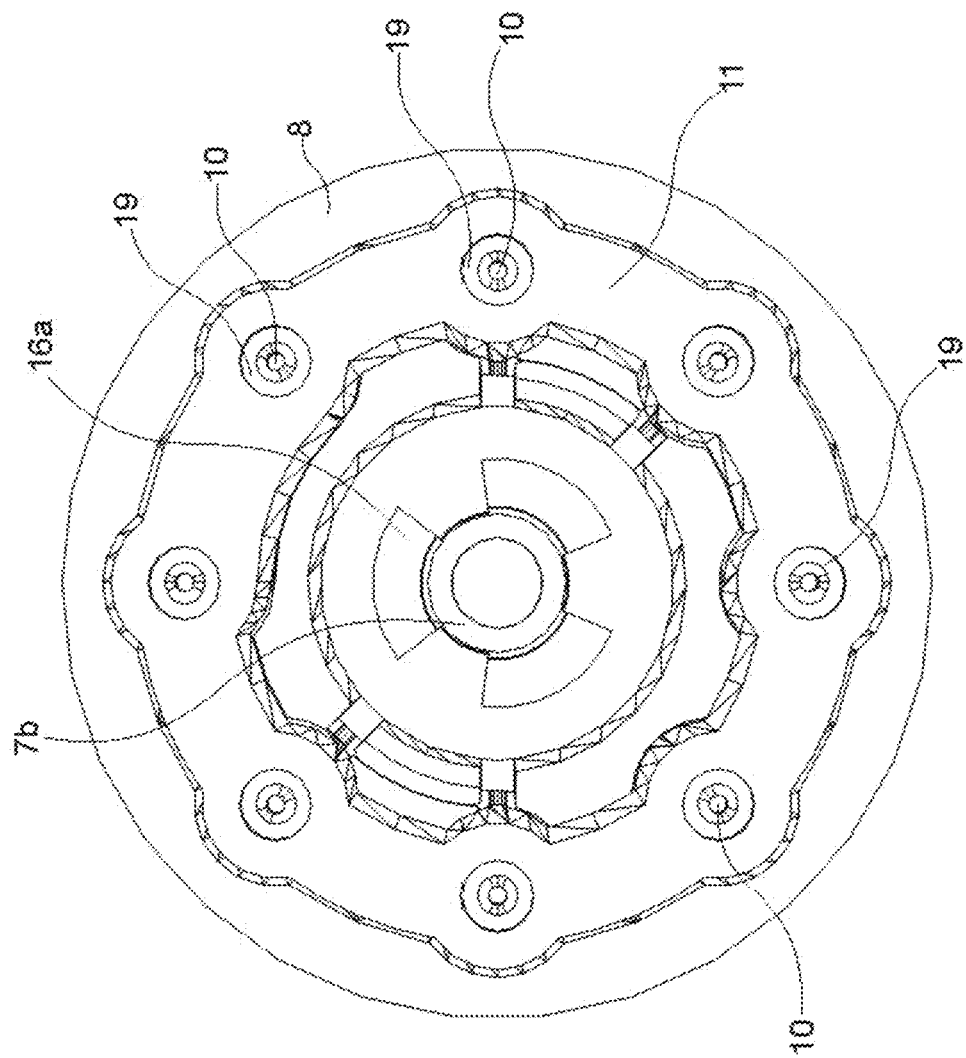
FIG. 9 is a view of the lancet magazine of the device according to the invention from below.

FIG. 9 shows the lancet magazine according to FIG. 8 again in a view from below. From this drawing, it can be seen that clip-like projections 156a, which can be deflected FIG. 9 shows the lancet magazine according to FIG. 8 again in a view from below. From this drawing, it can be seen that clip-like projections 156a, which can be deflected.

Figure 10:
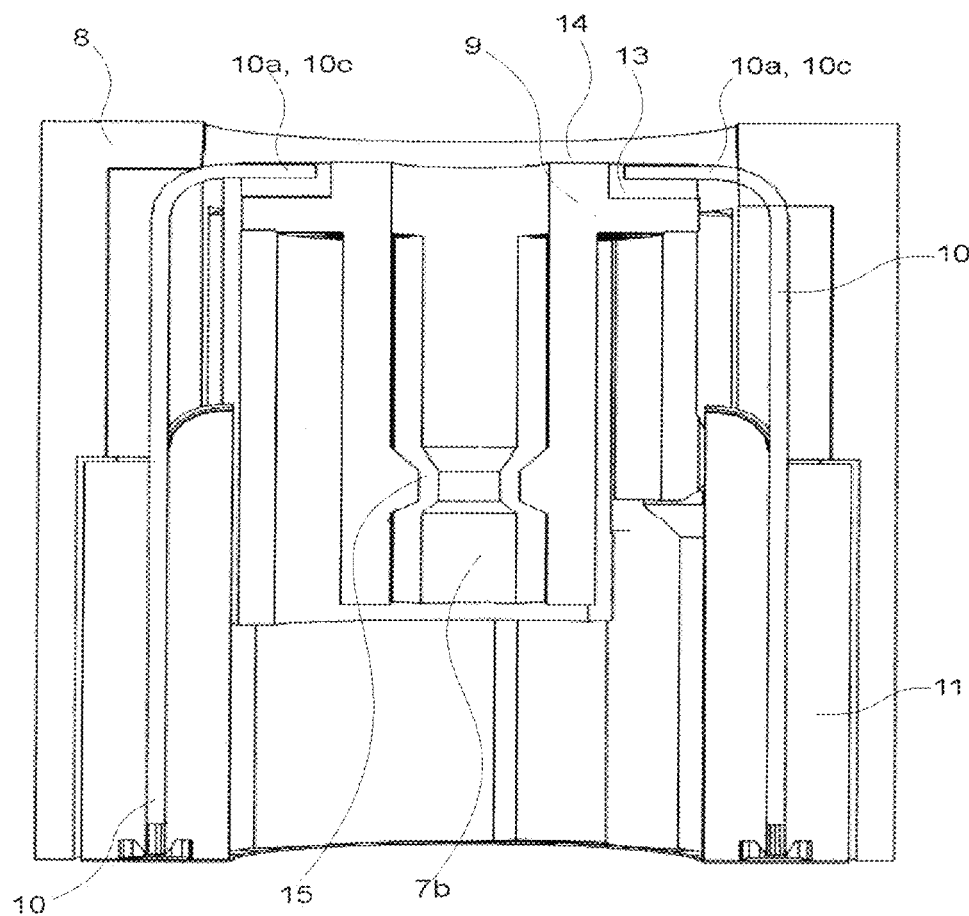
FIG. 10 is a cross-sectional drawing of the lancet magazine together with parts of the drive unit of the device according to the invention.

FIG. 10 is a sectional drawing, as seen in the longitudinal direction, of the lancet magazine together with parts of the drive unit of the device according to the invention. From this drawing, it can clearly be seen that the clip-like projections 16a of the first clip connection 16 can engage in a circular channel 16b of the part 7b of the plunger 7, so as to connect the lancet retraction unit 9 permanently to the drive unit, at least in the axial direction The upper ends 10c 10a of the lancets 10 are arranged engaging in a curved shape in the recesses 13 of the surface 14 of the retraction unit 9.

Figure 11:
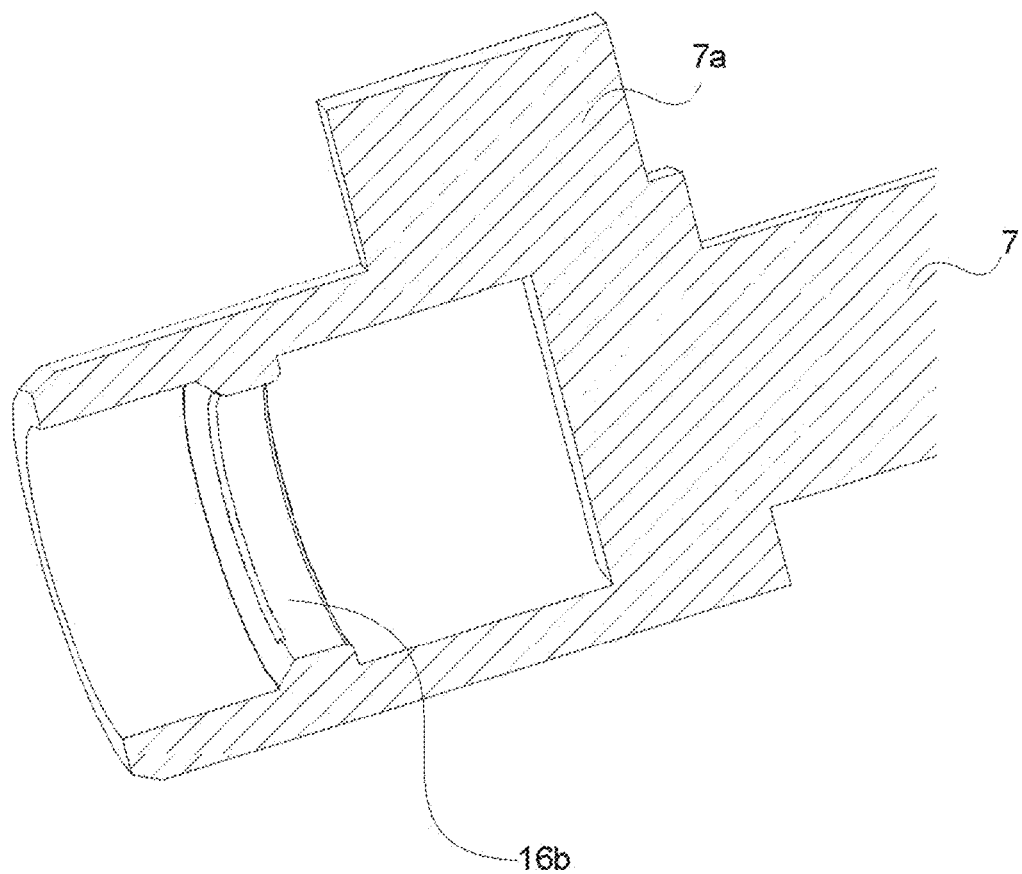
FIG. 11 is a perspective cross-sectional drawing of parts of the drive unit of the device according to the invention.

FIG. 11 is a perspective cross-sectional drawing of one possible embodiment of the plungers. From this drawing, it can be seen that the plunger-like element 7a is arranged on the outside of a cylinder shell part. At the same time, a channel is arranged inside the cylindrical shell in combination with a projection 16b, which serves to engage the clip-like projections (not shown here) of the retraction unit.

Certain features disclosed in the application are understood to be novel, including for example, features either individually or in combination with other features as compared with the prior art.

LIST OF REFERENCE NUMERALS 1 device for storing and supplying lancets
2 drive unit
3 lancet magazine
4 spring element
7 plunger
7a plunger-like element
7b cylindrical shell portion
7c base element
7d plunger end
7e twisted longitudinal axis of the lancet magazine
8 outer housing
9 retraction unit
10 lancets
10a curved end of the lancet unit
10b selected lancet
10c upper end of the lancet
11 lancet storage unit
13 depressions
13b forward movement inside the depression
14 surface
15a piercing direction
15b retraction direction
16 first clip connection
16a clip-like projection
16b projection or channel
17 second clip connection 17a clip-like projection
18 formed projection
19 continuous duct

The invention claimed is:

1. A device for storing and supplying lancets for obtaining bodily fluids, comprising:
   a lancet storage unit, having a plurality of needle-shaped lancets,
   a lancet magazine, which comprises a drive unit, which moves a selected lancet for carrying out a piercing process from a rest position into a piercing position in a piercing direction, and
   a retraction unit, which moves the selected lancet from the piercing position into the rest position in a retraction direction thereof after the piercing process has been carried out, the retraction unit being connected to the lancet storage unit and being displaceable as a whole with respect thereto,
   wherein the drive unit is attached to one spring element and loaded with a spring force by means of said one spring element, so as to move the drive unit and the retraction unit along the piercing direction and the retraction direction,
   wherein the drive unit is fixed with respect to the retraction unit by a first clip connection which connects the drive unit to the retraction unit rigidly along the piercing direction and the retraction direction, and through said first clip connection the drive unit is able to drive the entire forward and backward movement of the retraction unit and the selected lancet, and
   wherein the first clip connection is configured for twisting the drive unit with respect to the retraction unit about a longitudinal axis, extending in the piercing direction, of the lancet magazine, wherein by said twisting the next lancet is selected.

2. The device according to claim 1, wherein the lancet storage unit, which is in a cylindrical shell form and in which the plurality of needle-shaped lancets are arranged distributed mutually parallel on a circular path, encloses the retraction unit at least in part, whereby the retraction unit is cylindrical in form, and the retraction unit being displaceable inside the lancet storage unit.

3. The device according to claim 1, wherein the drive unit comprises at least one plunger-like element, a plunger end of which touches an end of the selected lancet during the piercing process and displaces the selected lancet in the piercing direction inside the lancet storage unit.

4. The device according to claim 3, wherein the plunger-like element is suitable for displacing the retraction unit with respect to the lancet storage unit.

5. The device according to claim 1, wherein the lancet storage unit is in the form of a cylindrical shell, wherein the cylindrical shell is provided with continuous ducts wherein each needle-shaped lancet is arranged inside such continuous duct.

6. The device according to claim 2, wherein the plurality of needle-shaped lancets each have a curved end so as each to engage in a depression, extending in a radial direction, on an end surface of the retraction unit, which is cylindrical in form.

7. The device according to claim 1, wherein the drive unit is in the form of a plunger-like element.

8. The device according to claim 7, wherein by said twisting the next lancet is selected by subsequently touching the end of the next lancet with the plunger-like element.

9. The device according to claim 7, comprising a second clip connection, which holds the retraction unit in a particular displacement position with respect to the lancet storage unit if all of the plurality of needle-shaped lancets are in the rest position.

10. The device according to claim 7, wherein the first clip connection is arranged between a cylinder portion of the plunger-like element and the inside of the retraction unit inside which the cylinder portion is located.

11. The device according to claim 10, wherein the first clip connection comprises at least one projection, which is able to be resiliently deflected by means of at least one plastics material arm and engage in a channel formed so as to be complementary thereto, wherein the channel is attached to the cylinder shell of the plunger-like element and the projections is fixed to the retraction unit, or vice versa.

12. The device according to claim 2, wherein the lancet magazine comprises an outer housing of cylindrical form in which the wherein the lancet storage unit together with a retraction unit are arranged.

13. The device according to claim 12, wherein the lancet magazine is entirety exchangeable and connectable with the drive unit without individual drive elements having to be present inside the lancet magazine.

14. The device according to claim 9 wherein the second clip connection is arranged between the retraction unit and the lancet storage unit and comprises at least one clip-like projections being connected to the retraction unit and at least one projection of a complementary form or a channel, in which the clip-like projection engages, being provided on the inside of the lancet storage unit.

15. The device according to claim 14, wherein the second clip connection, which is adapted so as to connect the retraction unit non-permanently to the lancet storage unit in the longitudinal direction of the device as a whole, serves, in a rest position in which the retraction unit is displaced upwards inside the lancet storage unit and none of the lancets is exiting the lower end of the lancet storage unit, to maintain a fastening of the retraction unit inside the lancet storage unit which is to be overcome by compression.

* * * * *